(12) United States Patent
Bracht et al.

(10) Patent No.: US 9,029,429 B2
(45) Date of Patent: May 12, 2015

(54) FISCHER-TROPSCH PROCESS

(71) Applicant: Shell Oil Company, Houston, TX (US)

(72) Inventors: Maarten Bracht, Amsterdam (NL); Martin Philipp Rohde, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/364,367

(22) PCT Filed: Dec. 10, 2012

(86) PCT No.: PCT/EP2012/074990
§ 371 (c)(1),
(2) Date: Jun. 11, 2014

(87) PCT Pub. No.: WO2013/087585
PCT Pub. Date: Jun. 20, 2013

(65) Prior Publication Data
US 2014/0350133 A1    Nov. 27, 2014

(30) Foreign Application Priority Data
Dec. 13, 2011    (EP) ..................................... 11193318

(51) Int. Cl.
| C07C 27/06 | (2006.01) |
| C07C 1/04 | (2006.01) |
| C01B 3/36 | (2006.01) |
| C01B 3/38 | (2006.01) |
| C10G 2/00 | (2006.01) |

(52) U.S. Cl.
CPC ... *C07C 1/04* (2013.01); *C01B 3/36* (2013.01); *C01B 3/382* (2013.01); *C01B 3/384* (2013.01); *C10G 2/32* (2013.01); *C01B 2203/0233* (2013.01); *C01B 2203/0244* (2013.01); *C01B 2203/0255* (2013.01); *C01B 2203/062* (2013.01); *C01B 2203/08* (2013.01); *C01B 2203/1241* (2013.01); *C01B 2203/1247* (2013.01); *C01B 2203/141* (2013.01); *C01B 2203/142* (2013.01); *C01B 2203/1671* (2013.01); *C01B 2203/168* (2013.01)

(58) Field of Classification Search
None
See application file for complete search history.

(56) References Cited

U.S. PATENT DOCUMENTS

| 6,525,104 | B2 | 2/2003 | Abbott | |
| 8,431,013 | B2 * | 4/2013 | Rojey et al. | 208/49 |
| 8,759,406 | B2 * | 6/2014 | Bracht et al. | 518/706 |
| 2007/0004809 | A1 | 1/2007 | Lattner et al. | |

FOREIGN PATENT DOCUMENTS

| EP | 1106570 | 6/2001 |
| EP | 1219566 | 3/2002 |
| EP | 1403216 | 3/2004 |
| WO | 9955618 | 11/1999 |
| WO | 0058242 | 10/2000 |
| WO | 2004041716 | 5/2004 |
| WO | 2007005126 | 1/2007 |
| WO | 2008017742 | 2/2008 |
| WO | 2010122025 | 10/2010 |
| WO | 2011073237 | 6/2011 |

OTHER PUBLICATIONS

Kuhre, C.J. et al.; "Partial Oxidation Grows Stronger in US"; Oil and Gas Journal, vol. 69, No. 36; pp. 86-90; Sep. 6, 1971.

* cited by examiner

*Primary Examiner* — Sudhakar Katakam

(57) ABSTRACT

The present invention is directed to a process for the production of hydrocarbon product from two different hydrocarbonaceous feedstocks comprising the steps of preparing a feed syngas having a hydrogen/carbon monoxide [$H_2/CO$] molar feed ratio suitable for Fischer-Tropsch synthesis, wherein the feed syngas is prepared by combining a first syngas having a $H_2/CO$ molar ratio below the molar feed ratio and a second syngas having a $H_2/CO$ molar ratio above the molar feed ratio; the first syngas is prepared from a liquid hydrocarbon comprising feedstock as the sole source of carbon in a first syngas manufacturing process comprising a non-catalytic partial oxidation step; the second syngas is prepared from a methane comprising feedstock as the sole source of carbon in a second syngas manufacturing process comprising a heat exchange reforming step and an auto-thermal reforming step; and the first and second syngas manufacturing processes are operated in parallel.

6 Claims, No Drawings

FISCHER-TROPSCH PROCESS

PRIORITY CLAIM

The present application is the National Stage (§371) of International Application No. PCT/EP2012/074990, filed Dec. 10, 2012, which claims priority from European application no. 11193318.0, filed Dec. 13, 2011, the disclosures of which are incorporated herein by reference.

The present invention relates to a process for the production of hydrocarbon products from two different hydrocarbon comprising feeds by means of a Fischer-Tropsch process.

EP-A-1219566 discloses an process for producing a synthesis gas (syngas) for a Fischer-Tropsch synthesis process by preparing a first synthesis gas from natural gas or another hydrocarbon feed in a partial oxidation reactor and a second synthesis gas in a steam methane reformer. The first syngas is fed directly into the Fischer-Tropsch synthesis process, whilst part of the second syngas is subjected to a separation treatment resulting in a carbon dioxide-rich gas and a carbon dioxide-depleted syngas. The carbon dioxide-rich gas is subsequently fed into the partial oxidation reactor and possibly also into the steam methane reformer. Such recycle of carbon dioxide requires a carbon dioxide separation unit, such as a pressure swing adsorption unit, and an additional compressor to compress the carbon dioxide-rich gas.

WO-A-2007/005126 discloses a process for producing synthesis gas blends which may be used as feed for a Fischer-Tropsch conversion process. In the process according to WO-A-2007/005126 the synthesis gas blend is prepared by mixing a syngas effluent stream from a steam reforming step with a syngas effluent from an oxygen-blown reforming step. The syngas effluent from the steam reforming step is compressed to a pressure substantially equal to that of the syngas effluent from the oxygen-blown reforming step before both syngas effluents are mixed into the synthesis gas blend that could be used as a feed to a Fischer-Tropsch conversion process. The feeds to the steam reforming step and to the oxygen-blown reforming step are both gaseous hydrocarbon streams, preferably derived from the same natural gas feedstock. The $H_2/CO$ molar ratio of the ultimate synthesis gas blend formed is higher than 1.9.

WO-A-2010/122025 discloses a process for preparing a feed syngas for use as a feed in a Fischer-Tropsch synthesis process, wherein a first syngas prepared in a partial oxidation process is combined with a second syngas prepared in a heat exchange reforming process. Both the partial oxidation process and the heat exchange reforming process are operated in parallel and use the same gaseous methane comprising feedstock. The first syngas has a hydrogen/carbon monoxide [$H_2/CO$] molar ratio below the $H_2/CO$ molar ratio of the feed syngas, whilst the second syngas has a $H_2/CO$ molar ratio above the $H_2/CO$ molar ratio of the feed syngas. As described in WO-A-2010/122025 the heat exchange reforming process is a high efficiency process for producing syngas resulting in better conversion, lower oxygen usage and lower carbon dioxide emissions.

The present invention aims to provide a process for the preparation of hydrocarbon products by means of a Fischer-Tropsch process using two different hydrocarbon Feedstocks—a gaseous feed and a liquid feed—without the need for a carbon dioxide recycle and hence without the need for additional gas separation and compression means required for such recycling. Using a liquid hydrocarbon feed as one of the feeds for the manufacturing of the syngas to be used in the Fischer-Tropsch synthesis reaction enables a better integration with a refinery by making use of refinery product streams, in particular the hydrocarbon residue streams from such refinery. Furthermore, the present invention aims to provide a process which enables specific finetuning of the hydrogen/carbon monoxide [$H_2/CO$] molar ratio of the feed syngas to the Fischer-Tropsch process. Yet another object of the present invention is to reap the benefits of the high efficiency of the heat exchange reforming process and the low inerts level of the process according to WO-A-2010/122025, whilst enabling the use of liquid hydrocarbon feed streams.

Accordingly, the present invention relates to a process for the production of hydrocarbon product from two different hydrocarbonaceous feedstocks comprising the steps of:
(a) preparing a feed syngas comprising hydrogen and carbon monoxide having a hydrogen/carbon monoxide [$H_2/CO$] molar feed ratio suitable for Fischer-Tropsch synthesis and
(b) using the feed syngas in a Fischer-Tropsch process using one or more syngas conversion reactors thereby obtaining the hydrocarbon product, wherein
(i) the feed syngas is prepared by combining a first syngas having a $H_2/CO$ molar ratio below the molar feed ratio and a second syngas having a $H_2/CO$ molar ratio above the molar feed ratio;
(ii) the first syngas is prepared from a liquid hydrocarbon comprising feedstock as the sole source of carbon in a first syngas manufacturing process comprising a non-catalytic partial oxidation step;
(iii) the second syngas is prepared from a methane comprising feedstock as the sole source of carbon in a second syngas manufacturing process comprising a heat exchange reforming step and an auto-thermal reforming step; and
(iv) the first syngas manufacturing process and the second syngas manufacturing process are operated in parallel.

The Fischer-Tropsch (FT) synthesis reaction is well known. In this reaction carbon monoxide and hydrogen react to form longer chain hydrocarbons and water. An industrial Fischer-Tropsch process may be operated in a single pass mode ("once through") or in a recycle mode. Carbon monoxide and hydrogen are usually fed into a Fischer-Tropsch process as a single gas referred to as synthesis gas or syngas.

The feed syngas prepared in step (a) and used in step (b) has a hydrogen/carbon monoxide [$H_2/CO$] molar feed ratio suitable for Fischer-Tropsch synthesis. Preferably this $H_2/CO$ molar feed ratio is in the range of from 1.6 to 2.1, more preferably from 1.8 to 2.0.

The Fischer-Tropsch process step (b) of the present invention could involve a single stage conversion process using a single syngas conversion reactor. It could also involve a multi-stage conversion process, which may involve, two, three or more conversion stages, generally two. Accordingly, the Fischer-Tropsch process step (b) of the present invention could be carried out in one syngas conversion reactor or in two or more, generally two, parallel syngas conversion reactors.

Preferably, the CO conversion level during each stage of a multi-stage conversion process is in the range 70-95%, and more preferably about 80-95%. Using a two stage process, a 80% CO conversion level at each stage provides an overall approximate 96% CO conversion level.

In one embodiment of the present invention the syngas conversion reactors comprise one or more fixed beds of Fischer-Tropsch catalyst. Such Fischer-Tropsch fixed bed catalyst are known in the art, and typically include a Group VIII metal component, preferably cobalt, iron and/or ruthenium, more preferably cobalt. Typically, the catalysts comprise a catalyst carrier. The catalyst carrier is preferably porous, such as a porous inorganic refractory oxide, more preferably alumina, silica, titania, zirconia or mixtures thereof and even more preferably titania.

References to the Periodic Table herein refer to the previous IUPAC version of the Periodic Table of Elements such as that described in the 68th Edition of the Handbook of Chemistry and Physics (CPC Press).

The optimum amount of catalytically active metal present on the carrier depends inter alia on the specific catalytically active metal. Typically, the amount of cobalt present in the catalyst may range from 1 to 100 parts by weight (ppw) per 100 ppw of carrier material, preferably from 10 to 50 ppw per 100 ppw of carrier material.

The catalyst suitably has an average diameter of 0.5-15 mm. One form of catalyst is as an extrudate. Such extrudates suitably have a length of 2-10 mm, and suitably a cross section of 1-6 mm$^2$, especially 2-3 mm$^2$.

The catalytically active metal may be present in the catalyst together with one or more metal promoters or co-catalysts. The promoters may be present as metals or as the metal oxide, depending upon the particular promoter concerned. Suitable promoters include oxides of metals from Groups IIA, IIIB, IVB, VB, VIB and/or VIIB of the Periodic Table, oxides of the lanthanides and/or the actinides. Preferably, the catalyst comprises at least one of an element in Group IVB, VB and/or VIIB of the Periodic Table, in particular titanium, zirconium, manganese and/or vanadium. As an alternative or in addition to the metal oxide promoter, the catalyst may comprise a metal promoter selected from Groups VIIB and/or VIII of the Periodic Table. Preferred metal promoters include rhenium, platinum and palladium.

A most suitable catalyst comprises cobalt as the catalytically active metal and manganese and/or vanadium as a promoter.

The promoter, if present in the catalyst, is typically present in an amount of from 0.1 to 60 ppw per 100 ppw of carrier material. It will however be appreciated that the optimum amount of promoter may vary for the respective elements which act as promoter. If the catalyst comprises cobalt as the catalytically active metal and manganese and/or vanadium as promoter, the cobalt: (manganese+vanadium) atomic ratio is advantageously at least 12:1.

In another embodiment the syngas conversion reactors are filled with a catalyst comprising a shaped porous structure and a catalytically active component loaded onto such porous structure. An example of such a catalyst system is disclosed in WO-A-2011/073237.

The Fischer-Tropsch synthesis is typically carried out at a temperature in the range from 125° C. to 350° C., more preferably 175° C. to 275° C., most preferably 200° C. to 260° C. The pressure typically ranges from 0.3 to 15.0 MPa, preferably from 0.3 to 10.0 MPa, more preferably 0.35 to 6.5 MPa.

The gaseous hourly space velocity may vary within wide ranges and is typically in the range from 500 to 10,000 Nl/l/h, preferably in the range from 1000 to 4,000 Nl/l/h.

It will be understood that the skilled person is capable to select the most appropriate conditions for a specific reactor configuration and reaction regime.

The first syngas is prepared from a liquid hydrocarbon comprising feedstock as the sole source of carbon in a first syngas manufacturing process comprising a non-catalytic partial oxidation step. Suitable feedstocks in this connection are heavy hydrocarbon feedstocks, in particular crude oil distillates, refinery oil residues and residues from catalytic hydroconversion processes. Examples include residual fuel oil or bunker C fuel oil, vacuum flashed cracked residues, visbreaker residues, asphalt, petroleum coke, vacuum residues and any combination of two or more of these. In general, the liquid feedstocks will have relatively high C/H weight ratios, typically of at least 6 and preferably of at least 8. For liquid hydrocarbon feedstocks the C/H weight ratio will not exceed 12, as at higher C/H weight ratios the feed would be solid.

In order to prepare the first syngas the liquid hydrocarbon comprising feedstock is subjected to partial oxidation in the first syngas manufacturing process. Such partial oxidation can take place according to various established processes. These processes include the Shell Gasification Process, which typically comprises a non-catalytic partial oxidation step followed by cooling of the syngas, thereby generating high pressure steam, and subsequent removal of soot (i.e. residual carbon and ash) from the syngas in a two-stage water scrubbing unit. A comprehensive survey of this process can be found in the Oil and Gas Journal, Sep. 6, 1971, pp 86-90. The partial oxidation in the sense of the present invention is a process wherein the syngas as obtained in the partial oxidation is not subsequently contacted with a reforming catalyst.

In the partial oxidation process the liquid hydrocarbon comprising feedstock is converted into syngas having a temperature of between 1100 and 1500° C. This stream is then reduced in temperature in for example a boiler. The pressure at which the syngas product is obtained in the partial oxidation may be between 3 and 12 MPa and suitably between 4 and 9 MPa, more suitably between 4.5 and 8 MPa. The pressure is suitably at the same level as the operating pressure of the syngas conversion reactor such to avoid expansion or recompression between the various process steps. However recompression may be required if a good match between the operating pressure levels cannot be achieved. Preferably no steam is added to the partial oxidation process.

The partial oxidation process is performed such to achieve an almost 100% conversion of the liquid hydrocarbon feed by combustion using a slight excess of oxygen. A slight excess is relative to the stoichiometric amount of oxygen required to perform a partial oxidation of the liquid hydrocarbon comprising feed. This excess of oxygen results in a syngas product having a $H_2$/CO molar ratio below the $H_2$/CO molar feed ratio, and especially in the range of from 0.3 to 1.5, more preferably from 0.7 to 1.0. The level of inerts in the first syngas will typically range between 3 and 8 mol %. Inerts, as used herein, is defined as the total of carbon dioxide ($CO_2$), nitrogen ($N_2$), methane ($CH_4$) and argon (Ar).

The oxygen used in the partial oxidation process as well as in the auto-thermal reforming step in the second syngas manufacturing process preferably has a purity of above 90 vol. % and more preferably above 99 vol. %. Such high purity is not only beneficial for the oxidation reaction, but also helps to keep the inerts level low. Such pure oxygen is preferably obtained in a cryogenic air separation process or by so-called ion transport membrane processes.

Before being combined with the second syngas, the first syngas is preferably first subjected to one or more treatments to remove any sour contaminants still present in the (raw) first syngas, in particular hydrogensulphide and any other sulphur-containing components as well as any nitrogen-containing sour components. Suitable gas treating methods are well known in the art and examples include the ADIP™ and ADIP-X™ process, the Claus process, HCN/COS hydrolysis process, SCOT™ process, Shell-Paques process, Sulferox™ process, Sulfinol™ process and Sulfinol-X process.

The second syngas is prepared from a methane comprising feedstock as the sole source of carbon in a second syngas manufacturing process comprising a heat exchange reforming step and an auto-thermal reforming step.

The methane comprising feedstock may be natural gas, associated gas or a mixture of $C_{1-4}$ hydrocarbons. The feed comprises mainly, i.e. more than 90 volume percent (% v/v), especially more than 94% v/v, $C_{1-4}$ hydrocarbons, and especially comprises at least 60% v/v methane, preferably at least 75% v/v, more preferably at least 90% v/v. Very suitably natural gas or associated gas is used. Suitably, any sulphur-containing components in the feedstock are removed before passing the feedstock into the second syngas manufacturing process. Such sulphur-containing components could suitably be removed by gas treating methods mentioned above.

The second syngas manufacturing process produces a syngas having a $H_2/CO$ molar ratio above the $H_2/CO$ molar feed ratio. Suitably the syngas as prepared in this second process has a $H_2/CO$ molar ratio in the range of from 1.9 to 2.8, preferably from 2.0 to 2.6. The inerts level of the second syngas is typically between 5 and 20 mol %, more preferably between 7 and 14 mol %.

The second syngas manufacturing process comprises a heat exchange reforming (HER) step performed in a HER unit and an auto-thermal reforming (ATR) step performed in an ATR unit. Such process is attractive because it has a high efficiency resulting in lower oxygen usage and lower $CO_2$ emissions in comparison with conventional steam reforming processes.

In one embodiment according to the invention part of the methane comprising feedstock and steam is fed to the HER unit and a second part is fed to the ATR unit. The effluent of the ATR unit, optionally in admixture with the effluent of the HER unit, is used to provide the necessary heat in the HER unit by means of indirect heat exchange. The parallel configured HER process may be performed as described in for example EP-A-1106570 or WO-A-2004/041716.

In another preferred embodiment of the invention the methane comprising feedstock and steam is for its majority or even more preferred, exclusively, fed to the HER unit. The effluent of the HER unit is used as feed in the ATR unit. The effluent of the ATR unit, in this configuration, is used to provide the necessary heat in the HER unit by means of indirect heat exchange. This so-called series process configuration is advantageous because a significant proportion of unconverted methane as is present in the effluent of the HER unit may then be converted in the ATR unit to carbon monoxide and hydrogen. The series configured HER process may be performed as described in for example U.S. Pat. No. 6,525,104.

The HER unit is preferably a tube and shell reactor wherein a steam reforming reaction takes place in the tubes in the presence of a steam reforming catalyst at low steam:carbon ratio and wherein the required heat of the endothermic reaction is provided by passing the effluent of the ATR unit to the shell side of the reactor. The catalyst and process conditions as applied in the steam reformer reactor tubes may be those known by the skilled person in the field of steam reforming. Suitable catalysts comprise nickel optionally applied on a carrier, for example alumina. The space velocity of the gaseous feed is preferably from 700 to 1000 liter (S.T.P.)/liter catalyst/hour, wherein S.T.P. means Standard Temperature of 15° C. and pressure of 1 atm abs. The steam to carbon (as hydrocarbon and CO) molar ratio is preferably in the range of from 0.1 to 2.5, more preferably between 0.2 and 1.5 and most preferably from 0.5 to 1.0.

The steam reforming catalyst is normally in the form of shaped units, e.g. cylinders, rings, saddles, and cylinders having a plurality of through holes, and are typically formed from a refractory support material e.g. alumina, calcium aluminate cement, magnesia or zirconia impregnated with a suitable catalytically active metal such as nickel. At low steam to carbon process ratios at least a portion of the catalyst preferably includes a precious metal such as ruthenium.

The product gas as it leaves the tubes of the HER unit preferably has a temperature of from 650 up to 900° C. and a $H_2/CO$ molar ratio of from 4 up to 6. The operating pressure at the tube side is preferably between 2 and 5 MPa. The ATR unit is typically operated at a slightly lower pressure to avoid recompression of the syngas from the HER unit before feeding to the ATR unit. This means that in the HER unit the pressure at the shell side will suitably be in this range as well.

The ATR unit may be the well-known auto-thermal reformer units as commercially used. The primary reformed product gas from the HER unit and oxygen are fed into the ATR unit, where the exothermic partial oxidation reaction takes place in the presence of a suitable catalyst. Such catalysts are well known in the art and examples can, for instance, be found in WO-A-2004/041716 and WO-A-2007/005126.

The product gas from the ATR unit, i.e. the second syngas, typically has a temperature of from 800 up to 1100° C. and, as described above, is used to provide the heat to the endothermic reaction in the HER unit. When leaving the HER unit the product gas from the ATR unit will typically have a temperature between 450 and 650° C. and a pressure between 3 and 10 MPa, usually between 3 and 5 MPa.

After subsequent cooling and, if necessary, removal of water, the second syngas is combined with the syngas as prepared in the first syngas manufacturing process to obtain the feed syngas for the Fischer-Tropsch synthesis. In one embodiment of the present invention the Fischer-Tropsch synthesis operation is carried out at a higher pressure of between 4.0 and 8.0 MPa. In this embodiment the second syngas is compressed from a pressure of below 5 MPa to the pressure of the first syngas to obtain a mixture of the first and second syngas having a pressure of between 5 and 10 MPa, which mixture is used without any further compression as the feed syngas to the syngas conversion reactor, where Fischer-Tropsch synthesis takes place. In another and more preferred embodiment the first and second syngas have similar pressures and are simply combined into a single syngas stream before being passed into the Fischer-Tropsch process step (b).

One of the main advantages of the present invention is that no recycle of carbon-containing streams (such as $CO_2$-rich stream or residual tail gas of the syngas conversion reactor) into the sungas manufacturing processes is required. The liquid hydrocarbon comprising feedstock and the methane comprising feedstock are the sole sources of carbon to, respectively, the first syngas manufacturing process and the second syngas manufacturing process. The desired $H_2/CO$ molar ratio of the feed syngas to the syngas conversion reactors can be attained by tailoring the amounts of the first and second syngas that are combined.

That which is claimed is:

1. A process for the production of hydrocarbon product from two different hydrocarbonaceous feedstocks comprising the steps of:
    (a) preparing a feed syngas comprising hydrogen and carbon monoxide having a hydrogen/carbon monoxide [$H_2/CO$] molar feed ratio suitable for Fischer-Tropsch synthesis and
    (b) using the feed syngas in a Fischer-Tropsch process using one or more syngas conversion reactors thereby obtaining the hydrocarbon product, wherein
        (i) preparation of the feed syngas comprises combining a first syngas having a $H_2/CO$ molar ratio below the molar feed ratio and a second syngas having a $H_2/CO$ molar ratio above the molar feed ratio;

(ii) preparation of the first syngas comprises a liquid hydrocarbon comprising feedstock as the sole source of carbon in a first syngas manufacturing process comprising a non-catalytic partial oxidation step;

(iii) preparation of the second syngas comprises a methane comprising feedstock as the sole source of carbon in a second syngas manufacturing process comprising a heat exchange reforming step and an auto-thermal reforming step; and (iv) the first syngas manufacturing process and the second syngas manufacturing process are operated in parallel.

2. A process according to claim 1, wherein the $H_2/CO$ molar feed ratio is in the range of from 1.6 to 2.1.

3. A process according to claim 1, wherein the first syngas has a $H_2/CO$ molar ratio in the range of from 0.3 to 1.5.

4. A process according to claim 1, wherein the second syngas has a $H_2/CO$ molar ratio in the range of from 1.9 to 2.8.

5. A process according to claim 1, wherein a first part of the methane comprising feedstock in the second syngas manufacturing process is fed to a heat exchange reformer (HER) unit in the heat exchange reforming step and a second part is fed to the autothermal reformer (ATR) unit in the autothermal reforming step and wherein the effluent of the ATR unit is used to provide the necessary heat in the HER unit by means of indirect heat exchange.

6. A process according to claim 1, wherein the methane comprising feedstock in the second syngas manufacturing process is exclusively fed to the HER unit and the effluent of the HER unit is used as feed to the ATR unit and wherein effluent of the ATR unit is used to provide the necessary heat in the HER unit by means of indirect heat exchange.

* * * * *